US006251885B1

(12) United States Patent
Osada et al.

(10) Patent No.: US 6,251,885 B1
(45) Date of Patent: Jun. 26, 2001

(54) CYTOTRIENINS, PROCESS FOR PREPARING THE SAME AND ANTI-TUMOR AGENT

(75) Inventors: Hiroyuki Osada; Hideaki Kakeya; Hui-ping Zhang; Kimie Kobinata, all of Wako (JP)

(73) Assignee: The Institute of Physical and Chemical Research, Wako (JP)

( * ) Notice: Subject to any disclaimer, the term of this patent is extended or adjusted under 35 U.S.C. 154(b) by 0 days.

(21) Appl. No.: 09/322,982

(22) Filed: Jun. 1, 1999

Related U.S. Application Data (63) Continuation of application No. PCT/JP97/04374, filed on Dec. 1, 1997.

(30) Foreign Application Priority Data

Nov. 29, 1996 (JP) .................................................. 8-320241

(51) Int. Cl.$^7$ ....................... C07D 225/06; A61K 31/415
(52) U.S. Cl. ............................................. 514/183; 540/461
(58) Field of Search .............................. 540/461; 514/183

(56) References Cited

U.S. PATENT DOCUMENTS 5,686,606 * 11/1997 Mizukami et al. .................. 540/461

FOREIGN PATENT DOCUMENTS

WO98/23594  4/1998 (JP) .

OTHER PUBLICATIONS

Patent Abstracts of Japan, vol. 14, No. 137 (C–0702), Mar. 15, 1990, JP 02–011573, Jan. 16, 1990.

Patent Abstracts of Japan, vol. 7, No. 191 (C–182), Aug. 20, 1983, JP 58–094393, Jun. 4, 1983.

Tetrahedron Letters (1997) vol. 38, No. 10, P. 1789–1792, "Novel Triene–ansamycins, Cytotrienins A and B, Inducing Apoptosis on Human Leukemia HL–60 Cells", Hui–ping Zhang et al.

The journal of Antibiotics (1997) vol. 50, No. 4, p. 370–372, "Cytotrienin A, a Novel Apoptosis Inducer in Human Leukemia HL–60 Cells," Hideaki Kakeya et al.

The Journal of Antibiotics (1993) vol. 46, No. 11, p. 1678–1686, "Novel Cytocidal Compounds, Oxopropalines from Streptomyces s. G324 producing Lavendamycin", , Naoki Abe et al.

The Journal of Antibiotics (1981) vol. 34, No. 11, P. 1402–1407, "Fredericamycin A. A New Antitumor Antibiotic", Dana J. Warnick–Pickle et al.

\* cited by examiner

*Primary Examiner*—Bruck Kifle
(74) *Attorney, Agent, or Firm*—Oblon, Spivak, McClelland, Maier & Neustadt, P.C.

(57) ABSTRACT

An anti-tumor composition containing cytotrienin (I), (II), (III) or (IV) as the active ingredient, which compounds are produced by culturing a bacterium which produces cytotrienin (I), (II), (III) or (IV), in a medium and accumulating cytotrienin (I), (II), (III) or (IV) in the medium and harvesting the product.

16 Claims, 9 Drawing Sheets

CYTOTRIENINS, PROCESS FOR PREPARING THE SAME AND ANTI-TUMOR AGENT

This application is a Continuation of international PCT application No. PCT/JP97/04374, Filed on Dec. 1, 1997.

BACKGROUND OF THE INVENTION

1. Field of the Invention

The present invention relates to cytotrienins I, II, III and IV, a process for preparing the same and anti-tumor agents containing the same as the active ingredient.

2. Description of the Background

Recent studies have demonstrated that many oncogene products act as signal transduction molecules and activation of such products induces neoplasia of cells. A number of oncogene products have been identified and it has now become clear that more than 50% of oncogenes encode tyrosine kinase, and these oncogenes are closely related to malignant transformation of cells and to retention of cancer morphology. Thus, it is considered that a compound which inhibits the functions of these oncogene products might be a potential anti-tumor agent and, hence, there is a need for additional anti-tumor agents having such a mode of action.

In addition, although many anti-tumor compounds have already been developed, a need still exists for additional anti-tumor agents having a new and different chemical structure.

SUMMARY OF THE INVENTION

Accordingly, it is an object of the present invention to provide compounds having anti-tumor activity, i.e., cytotrienins I, II, III and IV, a preparation method for the same and anti-tumor agents containing the same as the active ingredient.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The present invention is predicated, in part, upon the surprising discovery that Actinomyces sp. 95-74 strain which is a species of Streptomyces and was isolated from a soil sample collected in Shiki city, Saitama prefecture, Japan produces substances having anti-tumor activity.

The present invention provides cytotrienins I, II, III and IV represented by the following formulae.

Cytotrienins I, II, III and IV can be prepared by culturing a bacterium capable of producing cytotrienins, I, II, III and IV which belongs to Streptomyces species in a medium to produce and accumulate cytotrienins I, II, III and IV in the medium, and harvesting them. A preferable bacterium of the present invention includes Streptomyces sp. 95-74 strain.

Furthermore, the present invention provides an anti-tumor composition containing cytotrienin I, II, III or IV or a mixture thereof as the active ingredient.

The compounds of the present invention, cytotrienins I, II, III and IV are represented by the following formulas.

The present compounds cytotrienins I, II, III and IV can be produced from a microorganism of Streptomyces species, for example, Streptomyces sp. 95-74 strain. Streptomyces sp. 95-74 strain has the following mycological characteristics.

TABLE 1

Physiological characteristics of Streptomyces sp. 95-74 strain

| | |
|---|---|
| growth temperature | 12 ~ 38° C. |
| optimum temperature | 16 ~ 38° C. |
| cell wall composition | L,L-diaminopimelic acid |
| spore chain | spiral |
| surface of spore | plicated |
| color of aerial mycelium | gray ~ black |
| color of substrate mycelium | brown |
| soluble pigment | none |
| melanin pigment | none |

TABLE 2

Cultural feature of Streptomyces sp. 95-74 strain

| Medium | Color or Aerial Mycelium | Growth[*) | Color of Backside | Soluble Pigment |
|---|---|---|---|---|
| ISP-2 | dark gray (10 fe) | + + | ocher (2 ie) | none |
| ISP-3 | black (5 ih) | + + | light tan (2 ge) | none |
| ISP-4 | pearl (5 ba) | + | caramel (2 ea) | none |
| ISP-5 | gray (5 fe) | + | light tan (2 ge) | none |
| ISP-6 | dark gray (7 ih) | − ~ ± | caramel (2 ea) | none |
| ISP-7 | black coal (7 ml) | + + | mustard (21 g) | none |

*) + +: grown well, +: grown, ±: less grown, −: not grown

TABLE 3

Utilization of carbon source by Streptomyces sp. 95-74 strain

| Carbon Source | Growth*) |
|---|---|
| L-Arabinose | + |
| D-Xylose | + |
| D-Fructose | + |
| Sucrose | + + |
| i-inositol | + |
| L-rhamnose | + + |
| raffinose | + |
| D-mannitol | + + |
| Galactose | + |
| D-glucose | + + |

*) + +: utilize well, +: utilize, ±: almost not utilize, −: not utilize

Based on the microbial characteristics in the above Tables 1, 2 and 3, the bacterium strain of the present invention was identified as a Streptomyces species. This strain was deposited on Oct. 11, 1996, in the National Institute of Bioscience and Human Technology, Agency of Industrial Science and Technology, Japan (1-3, Higashi 1-chome, Tukuba City, Ibaraki Prefecture, Japan), which is an International Depository Authority, with the accession No. FERM BP-6185 under the provisions of the Budapest Treaty; all restrictions upon public access to the deposit will be irrevocably removed upon the grant of a patent on this application; and the deposit will be replaced if viable samples can not be dispensed by the depository.

The isolation of cytotrienins I, II, III and IV from fermentation broth of the above described actinomycete Streptomyces sp. 95-74 strain can be conducted according to culturing procedures for bacterium which belongs to Streptomyces species, but the details of the procedures will be described in the preparation examples below. After incubation, purification and isolation of cytotrienins I, II, III and IV from the culture broth can be conducted by utilizing the conventional means for collecting biological metabolite. For example, the mean includes use of a variety of ion exchange resin, nonionic adsorption resin, gel filtration chromatography, or chromatography or high performance liquid chromatography with adsorptive materials such as active carbon, alumina, silica gel, as well as crystallization, vacuum concentration and freeze-drying techniques. Each of these means can be utilized alone or in combination, or repeatedly.

Thus prepared novel cytotrienins I, II, III and IV shows anti-tumor activities as shown in the paragraph of "Evaluation study".

The applying method, dosage form and dosage amount of the anti-tumor agent of the present invention comprising cytotrienins I, II, III and IV as the active ingredient will be determined according to the purpose of the use of the agent.

For example, the anti-tumor agent of the present invention comprising cytotrienins I, II, III and IV as the active ingredient can be administered orally or parenterally. The dosage form includes, for example, oral medicines such as tablets, powders, capsules, granules, extracts, syrups and the like and parenteral medicines such as injections and suppositories. These preparations can be prepared by known methods using pharmaceutically acceptable additives such as vehicles and binders. The clinical dose of the anti-tumor agent of the present invention containing cytotrienins I, II, III and IV can be determined based on the age, weight, sensitivity and symptom of the patient. Generally, effective amount for one adult patient is approximately from 0.1 mg to 1 g per one day and this amount can be administered in a single dose or multiple doses. In addition, it is possible to use the amount outside of the above-described range, if necessary.

In addition, in the case that the compound is used as a reagent for chemical testing, cell growth is exhibited by administering the compound dissolved in organic solvent or aqueous organic solvent directly to each culture cell line. Such organic solvent includes, for example, methanol, and dimethylsulfoxide. Usage formulation includes, for example, solid such as powder and granule, and liquid dissolved in organic solvent or aqueous organic solvent. An amount of the agents containing cytotrienins I, II, III and IV as active ingredients effective to inhibit growth of tumor cell is generally from about $1\times10^{-3}$ to 100 µg/mL. However, suitable amount would vary depending on the kind of culture cell line or the purpose of the compound to be used. It is possible to use an amount out of the above-described range, if necessary.

EXAMPLES

Reference will now be made to certain examples which are provided solely for purposes of illustration and are not intended to be limitative:

Preparation Example 1

Streptomyces sp 95-74 strain was inoculated on a medium (pH 6.5) composed of 2% of glucose, 2.5% of soy flour, 1% of soluble starch, 0.4% of yeast, 0.1% of broth, 0.2% of salt and 0.005% of dipotassium hydrogen phosphate, and then incubation with shaking was continued for 96 hours at 28° C.

Culture broth (1.8 L) was extracted with 2 L of 80% acetone. After vacuum filtration and vacuum concentration, the aqueous solution was adjusted to pH 7.0 and was extracted three times with 2.6 L of ethyl acetate. Ethyl acetate phases were combined and then concentrated under reduced pressure to obtain 571 mg of brown syrup.

The syrup (571 mg) was dissolved in 1 ml of ethyl acetate/methanol (9:1) and applied on a silica gel column (which is composed of commercially available Sep-Pak® CARTRIDGE PLUS SILICA (diameter 10 mm, length 30 mm) connected to packed column (10 ml injection syringe) (Silica gel: diameter 20 mm, length 50mm)) which was previously treated with ethyl acetate/methanol (9:1). The ratio of ethyl acetate and methanol was changed (90:10, 50:50) and 60 ml of each solution was eluted. Finally, 60 ml of methanol was eluted. The active component was eluted in the fraction of ethyl acetate-methanol (90:10). The fractions were concentrated under reduced pressure to obtain 484 mg of brown oily material.

Then, the material was purified by preparative high performance liquid chromatography using ODS column (diameter 20 mm, length 250 mm; capsule pack, Shiseido) and 62.5% aqueous methanol as eluent under conditions that the flow rate was 9.0 mL/min and detection wavelength was 230 mm. As the result, 64.4 mg and 9.8 mg of cytotrienins I and II were obtained as light yellow powder, respectively.

Figure 1:
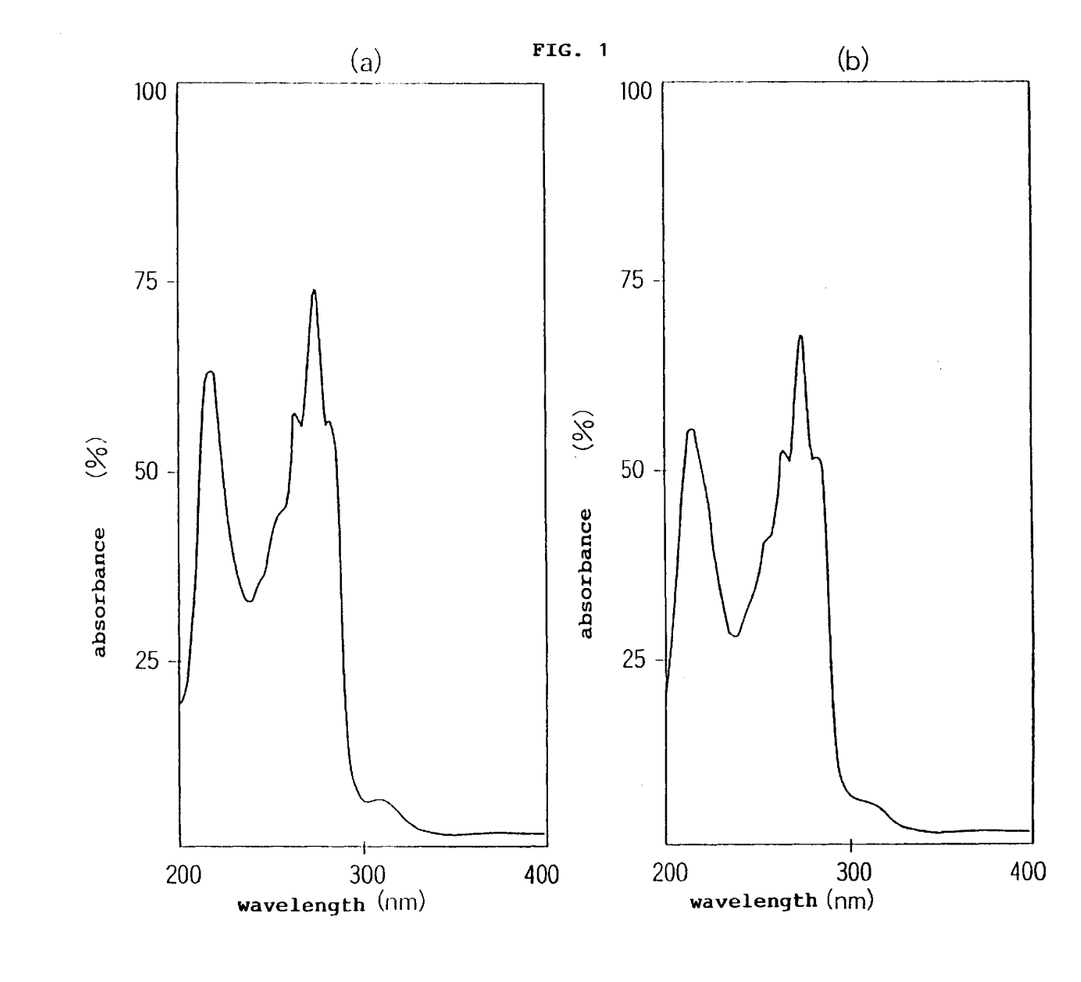
FIG. 1 is a UV spectrum of cytotrienins I (FIG. 1a) and II (FIG. 1b) in methanol.
Figure 2:
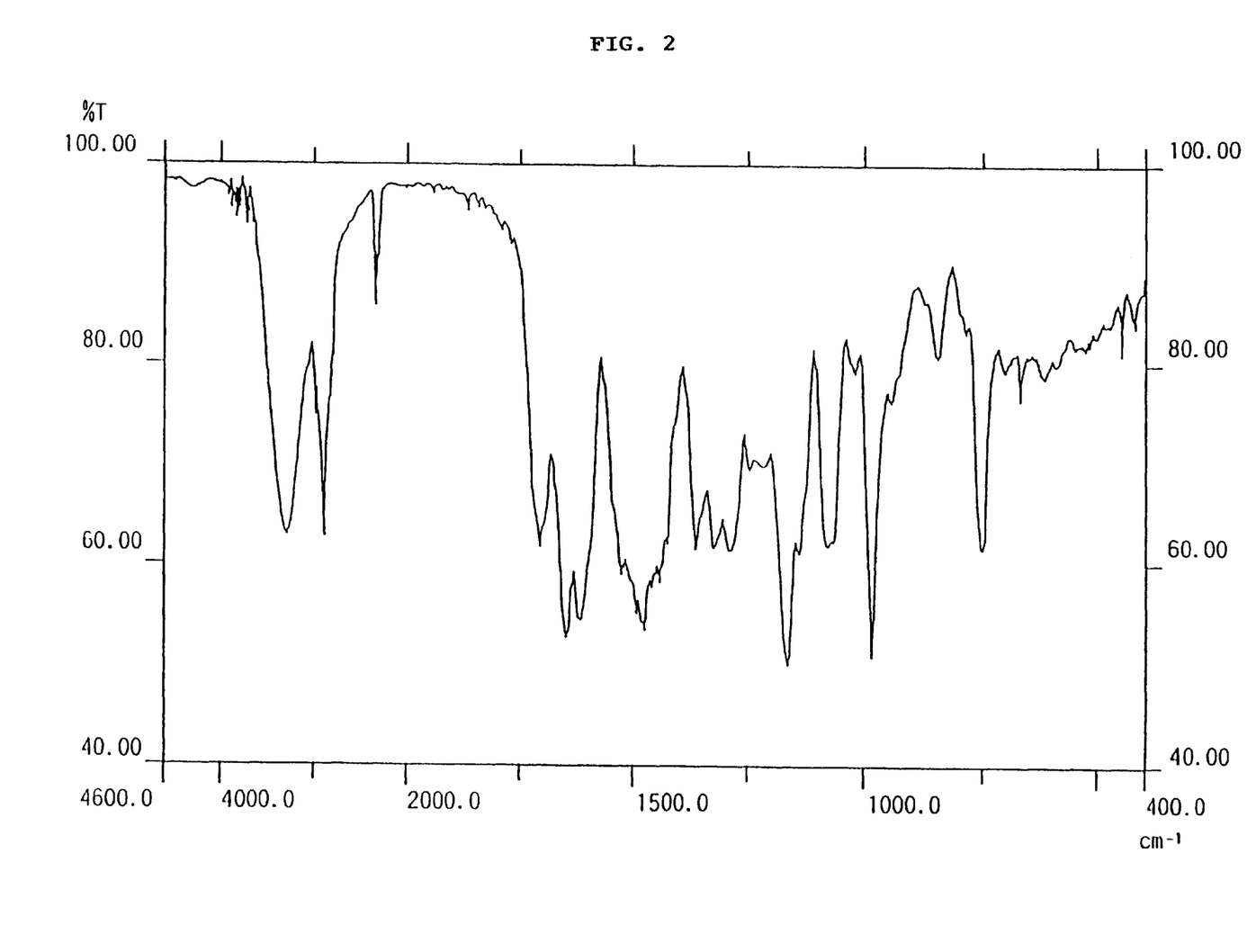
FIG. 2 is an infrared spectrum (KBr) of cytotrienin I.
Figure 3:
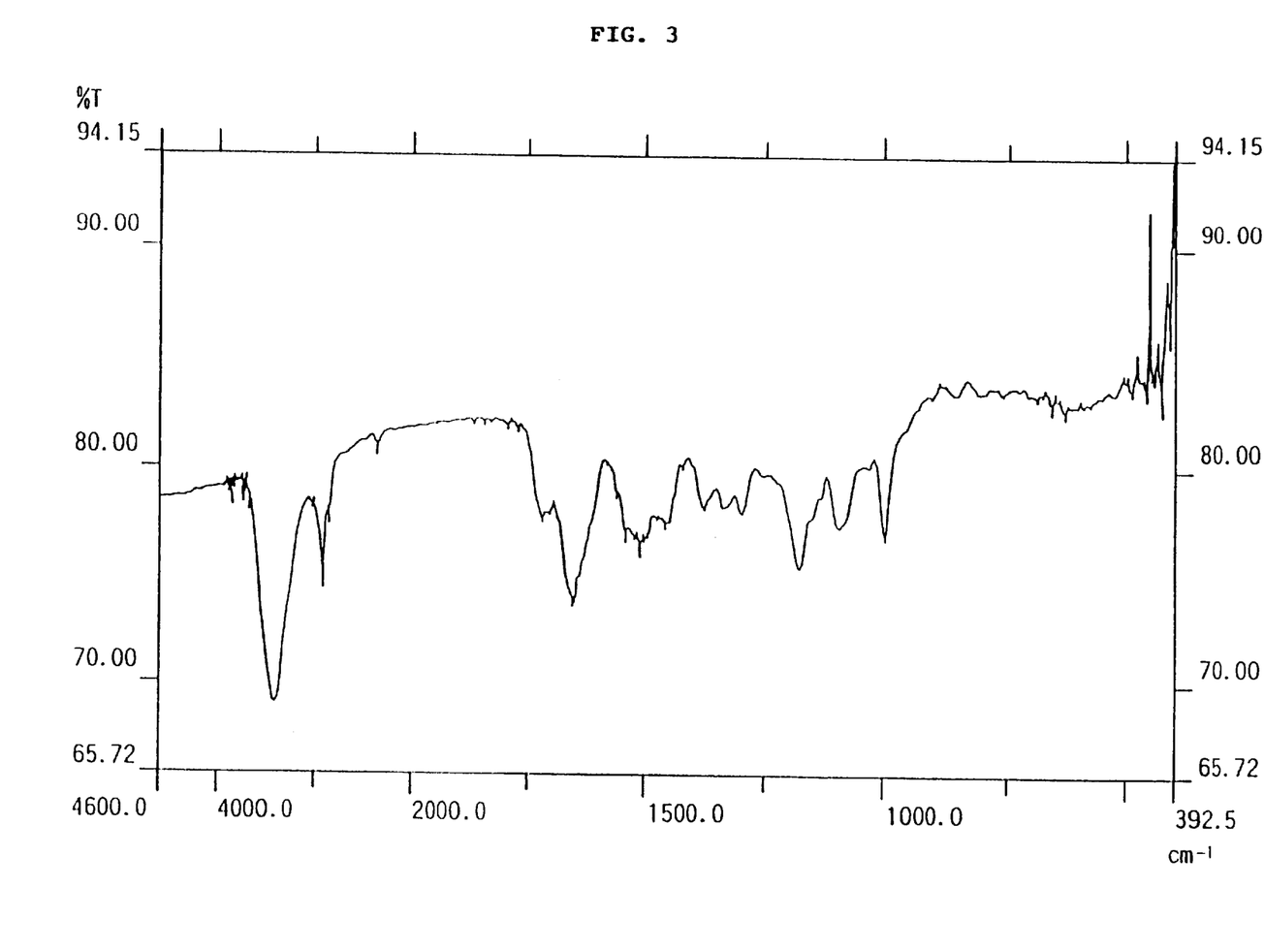
FIG. 3 is a infrared spectrum (KBr) of cytotrienin II.
Figure 4:
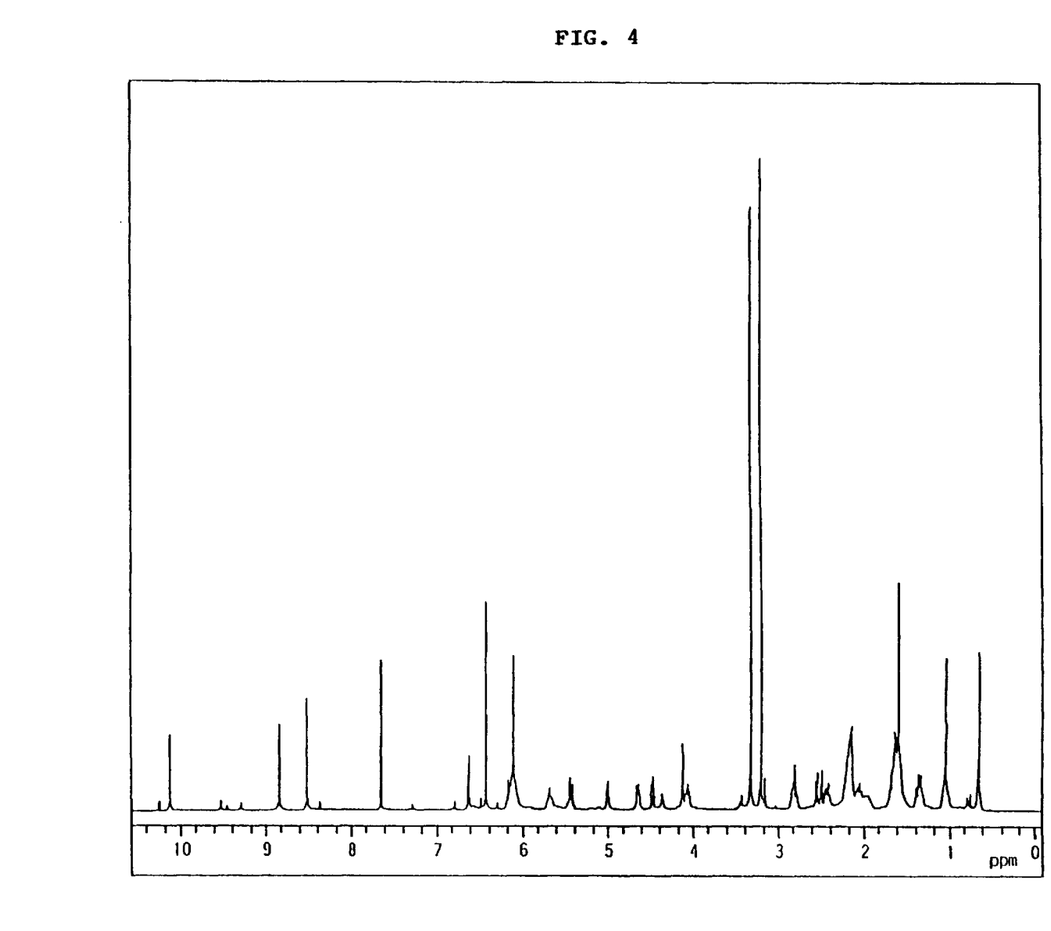
FIG. 4 is a $^1$H NMR spectrum (DMSO-$d_6$) of cytotrienin I.
Figure 5:
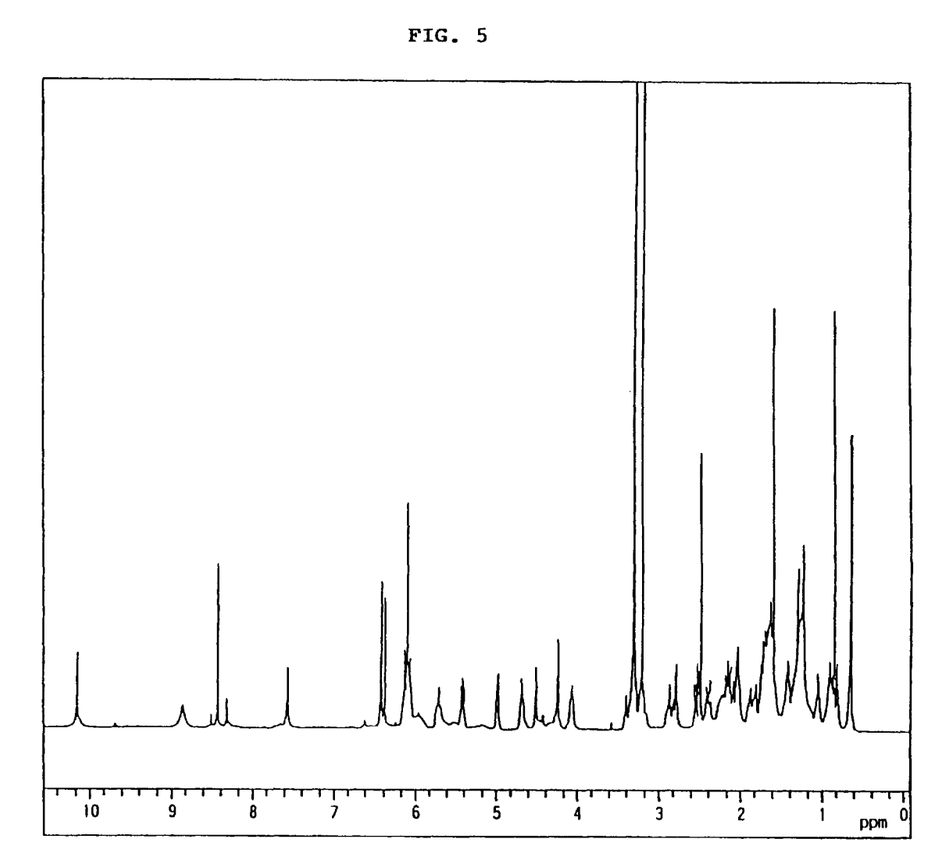
FIG. 5 is a $^1$H NMR spectrum (DMSO-$d_6$) of cytotrienin II.
Figure 6:
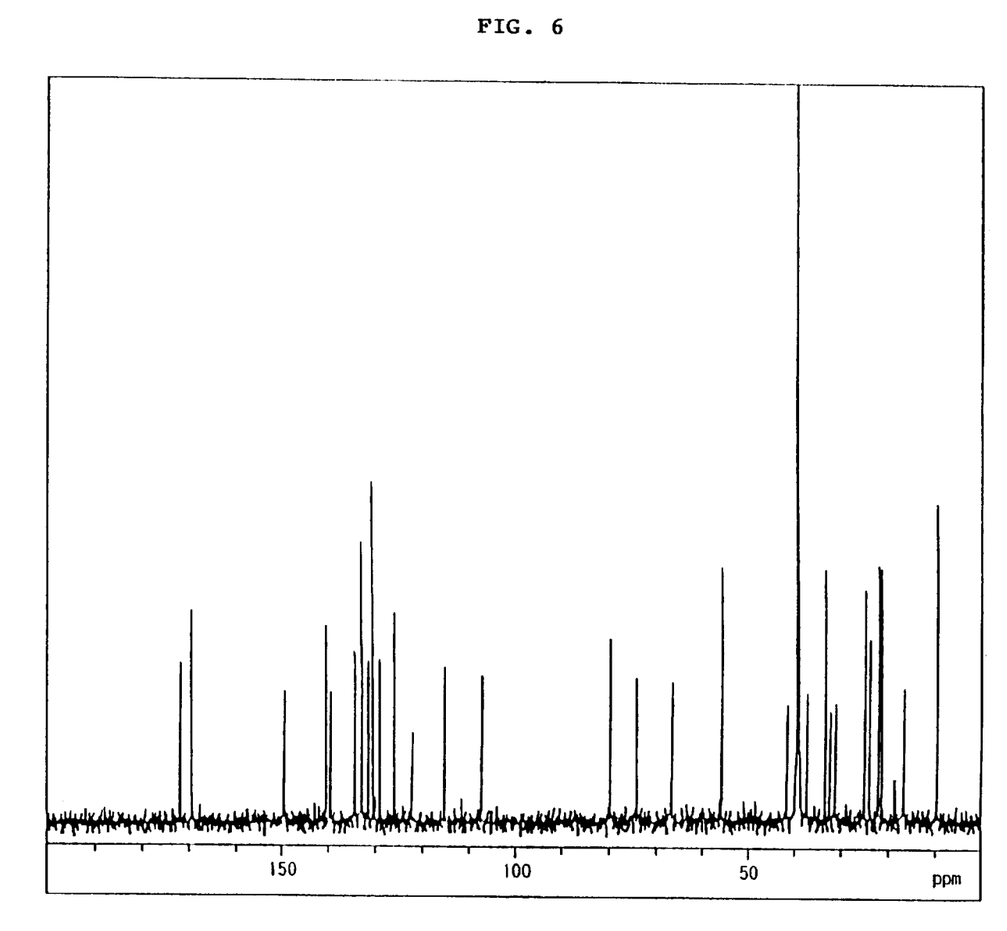
FIG. 6 is a $^{13}$C NMR spectrum (DMSO-$d_6$) of cytotrienin I.
Figure 7:
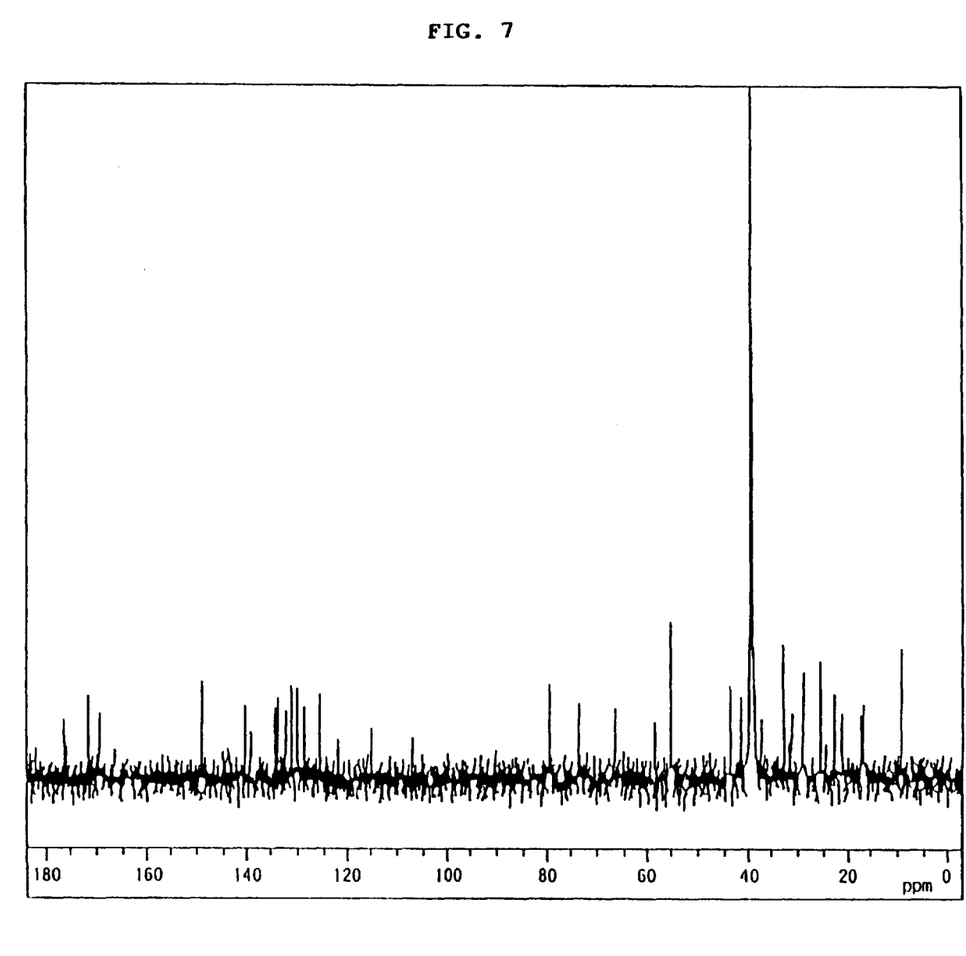
FIG. 7 is a $^{13}$C NMR spectrum (DMSO-$d_6$) of cytotrienin II.
Figure 8:
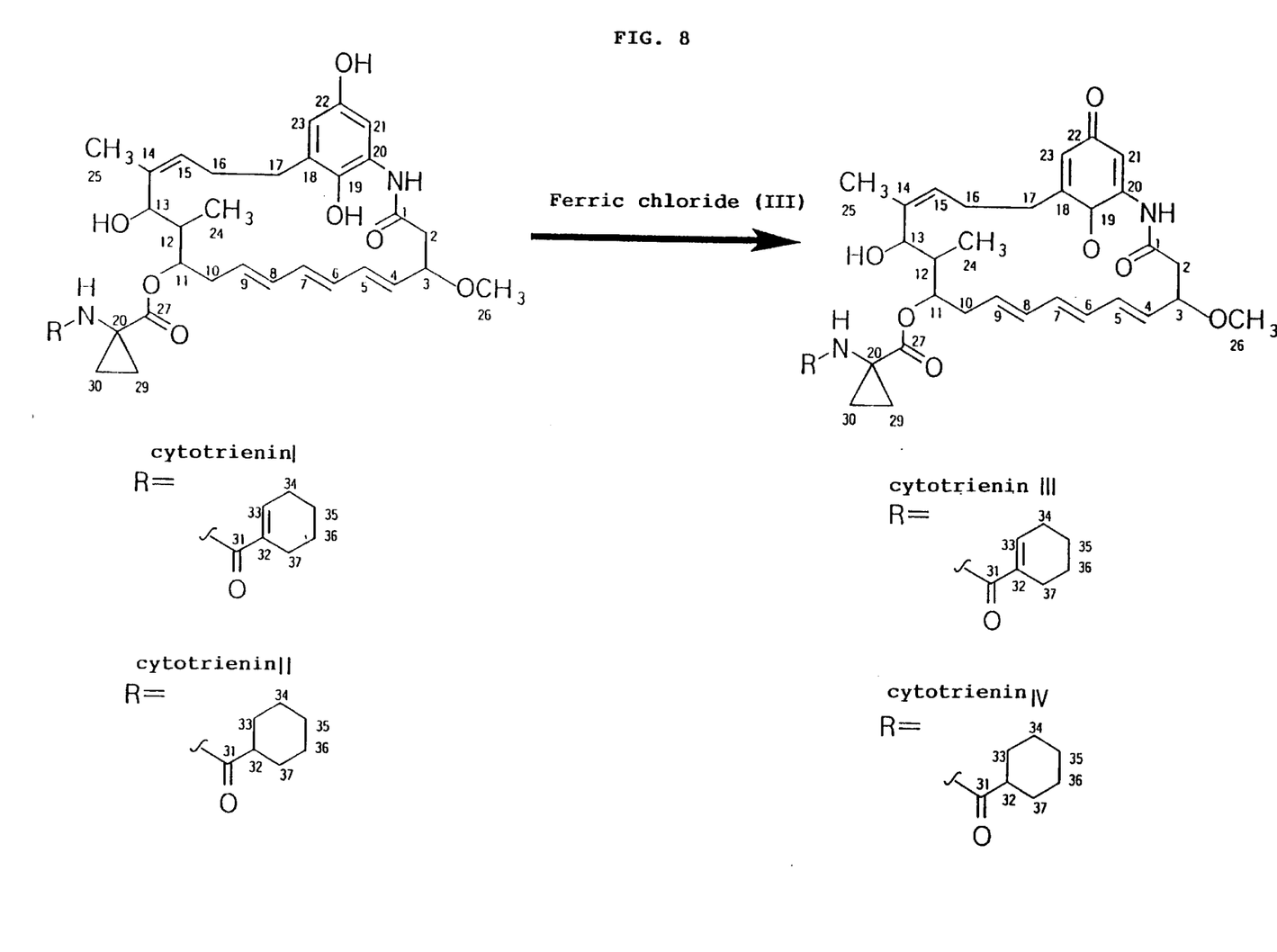
FIG. 8 illustrates conversion of cytotrienins I and II to III and IV, respectively.
Figure 9:
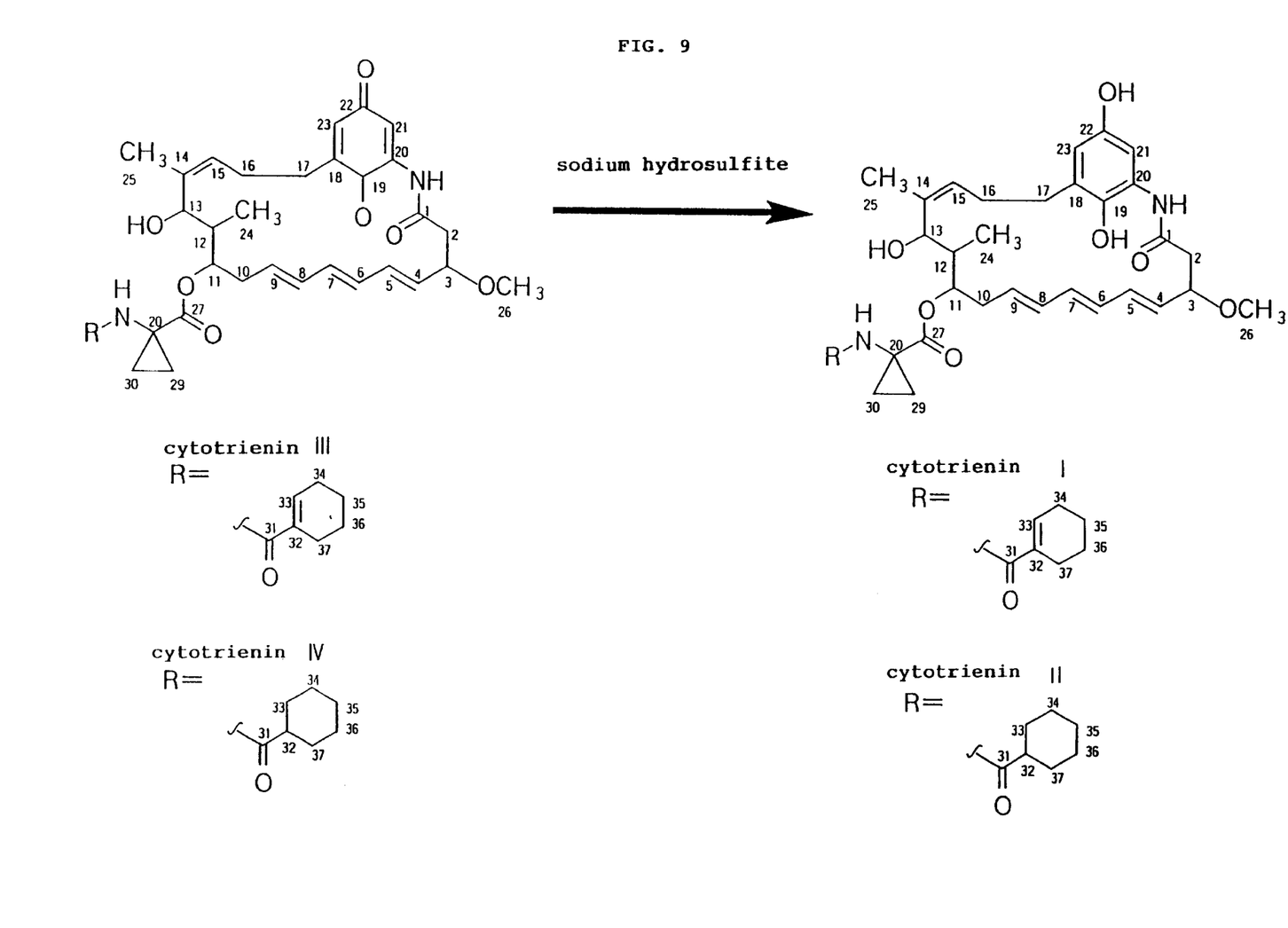
FIG. 9 illustrates conversion of cytotrienins III and IV to I and II, respectively.

Although cytotrienins III and IV can be isolated from the culture products by the same purification procedures, these compounds can be easily obtained by oxidizing cytotrienins I and II with ferric chloride (III) (FIG. 8). In addition, cytotrienins III and IV can be converted to cytotrienins I and II through reductive reaction with sodium hydrosulfite (FIG. 9).

Physiological features of the purified authentic cytotrienins I, II, III and IV are shown in Tables 4 and 5 and NMR spectral data of cytotrienins I and II are shown in Tables 6 and 7.

TABLE 4

Physiological characteristics of cytotrienins I and II

| | Cytotrienin I | Cytotrienin II |
|---|---|---|
| Appearance | light yellow powder | light yellow powder |
| Melting point | 132–135 ° C. | 163–165° C. |
| $[\alpha]_D^{25}$ | +270.6(c 1.00, MeOH) | +211.2(c 1.00, MeOH) |
| Molecular formula | $C_{37}H_{48}N_2O_8$ | $C_{37}H_{50}N_2O_8$ |
| Mass spectra | $(M + H)^+$ | $(M + H)^+$ |
| FABMS (pos.) | 649 | 651 |
| HRFABMS (pos.) | | |
| found (m/z) | 649.3616 | 651.3704 |
| calculated (m/z) | 649.3498 | 651.3646 |
| UV $\lambda_{max}^{MeOH}$nm($\epsilon$) | 214 (41560), 262 (35780), 273 (46100), 283 (35330), | 260 (31590), 271 (39450), 282 (30550) |
| IR$\gamma_{max}^{KBr}$cm$^{-1}$ | 3400, 1720, 1660, 1650, 1490, 1180, 1000, 850 | 3400, 1720, 1660 1650, 1500, 1180 1000 |

TABLE 5

Physiological characteristics of cytotrienins III and IV

| | Cytotrienin III | Cytotrienin IV |
|---|---|---|
| Appearance | light yellow powder | light yellow powder |
| Molecular formula | $C_{37}H_{46}N_2O_8$ | $C_{37}H_{46}N_2O_8$ |
| Mass spectra | $(M + H)^+$ | $(M + H)^+$ |
| FABMS (pos.) | 647 | 649 |

TABLE 6

400 MHz $^1$H NMR and 100 MHz $^{13}$C NMR chemical shift ($\delta$ppm)[1] data for cytotrienin I

| Position | $^{13}$C | $^1$H (J/Hz) | Position | $^{13}$C | $^1$H (J/Hz) |
|---|---|---|---|---|---|
| 1 | 169.46 s | — | 19-OH | 125.90 s | 7.62 s[2] |
| 2 | 41.69 t | 2.80 m 2.54 | 20 20-NH | — | 10.06 s[2] |
| 3 | 79.88 d | 4.01 m | 21 | 107.08 d | 6.40 s[3] |
| 4 | 130.39 d | 5.40 dd (15.1, 8.8) | 22 | 149.27 s | — |

TABLE 6-continued

400 MHz $^1$H NMR and 100 MHz $^{13}$C NMR chemical shift (δppm)[1] data for cytotrienin I

| Position | $^{13}$C | $^1$H (J/Hz) | Position | $^{13}$C | $^1$H (J/Hz) |
|---|---|---|---|---|---|
| 5 | 134.49 d | 6.13 dd (15.1, 9.7) | 22-OH | — | 8.82 s[2] |
| 6 | 128.95 d | 6.07 dd (14.7, 9.6) | 23 | 115.29 d | 6.40 s[3] |
| 7 | 134.09 d | 6.09 dd (14.7, 8.7) | 24 | 9.22 q | 0.64 d (6.8) |
| 8 | 132.50 d | 6.01 dd (15.0, 8.7) | 25 | 20.99 q | 1.60 s |
| 9 | 130.39 d | 5.62 td (15.0, 10.7, 4.4) | 26 | 55.69 q | 3.20 s |
| 10 | 32.44 t | 2.44 dt (10.7, 3.4) | 27 | 171.64 s | — |
|  |  | 2.16 m | 28 | 33.31 s | — |
| 11 | 74.30 d | 4.61 dq (10.3, 4.8, 2.0) | 28-NH | — | 8.49 s[2] |
| 12 | 37.48 t | 1.66 m | 29 | 16.68 t | 1.35 m |
| 13 | 66.69 d | 4.41 brs | 30 | 16.45 t | 1.04 m |
| 13-OH |  | 4.11 d[2] (5.4) | 31 | 169.26 s | — |
| 14 | 139.38 s | — | 32 | 133.01 s | — |
| 15 | 122.12 d | 4.99 brd (7.8) | 33 | 132.68 d | 6.59 m |
| 16 | 25.02 t | 2.16 m | 34 | 24.81 t | 2.16 m |
| 17 | 31.24 t | 2.82 m |  |  | 1.94 m |
|  |  | 2.04 m | 35 | 21.24 t | 1.60 m |
| 18 | 131.39 s | — | 36 | 21.79 t | 1.60 m |
| 19 | 140.29 s | — | 37 | 23.75 t | 2.16 m |

1) Data was obtained in DMSO-$d_6$
2) The signal is exchanged with deuterium in $D_2O$
3) The signal shows the following data in deuterated methanol;
$\delta_{H-21}$ 6.52 (J=2.9 Hz), $\delta_{H-23}$ 6.48 (J=2.9 Hz)

TABLE 7

400 MHz $^1$H NMR and 100 MHz $^{13}$C NMR chemical shift (δppm)[1] data for cytotrienin II

| Position | $^{13}$C | $^1$H (J/Hz) | Position | $^{13}$C | $^1$H (J/Hz) |
|---|---|---|---|---|---|
| 1 | 169.52 s | — | 20-OH | — | 10.07 s[2] |
| 2 | 41.69 t | 2.76 dd (13.2, 4.9) | 21 | 107.09 d | 6.32 brd (2.4) |
|  |  | 2.51 m | 22 | 149.23 s | — |
| 3 | 79.88 d | 4.02 td (10.7, 4.9) | 22-OH | — | 8.26 ds[2] |
| 4 | 130.38 d | 5.35 dd (15.1, 8.8) | 23 | 115.50 d | 6.37 brd (2.4) |
| 5 | 134.61 d | 6.09 dd (15.1, 8.3) | 24 | 9.16 q | 0.59 d (6.8) |
| 6 | 128.96 d | 6.04 dd (16.1, 8.3) | 25 | 21.06 q | 1.55 s |
| 7 | 134.05 d | 5.95 dd (16.1, 7.8) | 26 | 55.71 q | 3.17 s |
| 8 | 132.53 d | 604 dd (15.0, 7.8) | 27 | 171.66 s | — |
| 9 | 130.51 d | 5.67 td (15.1, 10.3, 3.9) | 28 | 32.84 s | — |
| 10 | 32.56 t | 2.35 dt (9.3, 4.9) | 28-OH | — | 8.49 s[2] |
|  |  | 2.16 m | 29 | 16.68 t | 1.20 m |
| 11 | 74.17 d | 4.63 brd (10.3) | — | — | 0.99 m |
| 12 | 37.38 d | 1.62 m | 30 | 17.17 t | 1.38 m |
| 13 | 66.85 d | 4.44 brs | — | — | 1.28 m |
| 13-OH | 4.19 d[2] | (5.4) | 31 | 176.43 s | — |
| 14 | 139.41 s | — | 32 | 43.69 d | 2.06 td (8.3,3.4) |
| 15 | 122.08 d | 4.92 brd (7.3) | 33 | 29.23 t | 1.68 m |
| 16 | 25.02 t | 2.16 m | — | — | 1.57 m |
| 17 | 31.27 t | 2.84 m | 34 | 25.39 t | ~1.62 m |
|  |  | 1.99 m | 35 | 25.49 t | ~1.16 m |
| 18 | 131.49 s | — | 36 | 25.50 t | ~1.16 m |
| 19 | 140.63 s | — | 37 | 28.90 t | ~1.82 m |
| 19-OH | — | 7.50 s[2] |  |  | 1.19 m |
| 20 | 125.87 s | — |  |  |  |

1) Data was obtained in DMSO-$d_6$
2) The signal is exchanged with deuterium in $D_2O$ Biological activities of the compounds of the present invention were determined as described below.

Evaluation Study 1

Activity of cytotrienins I, II, III and IV to revert v-src $^{ts}$-NRK cell (rat renal cell infected with temperature-sensitive Rous sarcoma virus) to normal morphology.

Many oncogenes encode tyrosine kinase. Among them, v-src is believed to encode non-receptor type tyrosine kinase to induce the cell to transformed morphology. V-src$^{ts}$-NRK cell, wherein temperature-sensitive V-SRC gene is transformed, shows cancer morphology at permissive temperature (32° C.) and shows normal morphology at non-permissive temperature (39° C.). This indicates that the agent which induces normal morphology inhibits the function of SRC protein and signal transduction system concerned to SRC protein and inhibits the proliferation of cancer cells selectively.

V-src$^{ts}$-NRK cell is typically cultured on Eagle's MEM medium containing 10% of bovine serum at 32° C. in a culture chamber which is saturated with 5% of carbon dioxide and steam. At the permissive temperature (32° C.), a series of diluted cytotrienin I, II, III and IV were added. After 18 hours, inducibility to normal morphology was analyzed. The result was shown in Table 8.

TABLE 8

The reversion activity of cytotrienins I, II, III and IV
to induce v-src$^{ts}$-NRK cell to normal morphology

| concentration | Cytotrienins | | | |
|---|---|---|---|---|
| (µg/ml) | I | II | III | IV |
| 0.1 | + | + | + + | + + |
| 0.3 | + + | + | + + + | |
| 1 | + + + | + + + | + + + | + + + |
| 3 | + + + | + + + | + + + | + + + |
| 10 | + + + | + + + | + + + | + + + |

+: weakly induce normal morphology
+ +: induce normal morphology
+ + +: highly induce normal morphology Table 8 shows that cytotrienins I, II, III and IV are each effective as an anti-tumor agent.

Evaluation Study 2

Inhibitory activity for cell cycle of cytotrienins I, II, III and IV.

Generally cell divides and proliferates in accordance with a cell cycle including a series of phases such as M phase, G1 phase, S phase and G2 phase. If something happens in the control mechanism of cell cycle, homeostasis breaks and possibility of suffering from cancer or immune disease would increase.

V-src$^{ts}$-NRK cell, wherein temperature-sensitive SRC gene is transformed, shows cancer morphology at permissive temperature (32° C.) and many cells in S phase are observed, while at non-permissive temperature (39° C.) the cell shows normal morphology and many cells in G0/G1 phase are observed. This indicates that an agent which interrupts the progress of S phase at permissive temperature and induces to normal morphology inhibits the function of SRC protein and signal transduction system related to SRC protein as well as the proliferation of cancer cells selectively.

When v--src$^{ts}$-NRK cell is cultured at non-permissive temperature (39° C.), the cell cycle stops at G0/G1 phase and if the temperature is downshifted to permissive temperature (32° C.), the cell advances to S phase and then repeats the proliferation. A series of diluted cytotrienin I, II, III and IV were added simlutaneously with the downshift and, after 18 hours, the advancement of cell cycle to S phase was analyzed by flow cytometry. The results are shown in Table 9.

TABLE 9

Inhibition effect of cytotrienins I, II, III and IV
on v-src$^{ts}$-NRK cell cycle

| concentration | Cytotrienins | | | |
|---|---|---|---|---|
| (µg/ml) | I | II | III | IV |
| 0.03 | + | + | + + | + + |
| 0.1 | + + | + + | + + + | + + + |
| 0.3 | + + + | + + + | + + + | + + + |
| 1 | + + + | + + + | + + + | + + + |
| 3 | + + + | + + + | + + + | + + + |

+: weakly inhibits the progress of S
+ +: inhibits the progress of S phase
+ + +: strongly inhibits the progress of S phase Table 9 shows that cytotrienins I, II, III and IV are effective as anti-tumor agent.

Evaluation Study 3

Inhibitory activity for proliferation of cancer cells of cytotrienins I, II, III and IV.

Human leukocyte cells K562 and HL-60 were incubated on PRM 1640 medium (comprising 10% of bovine serum) in a culture chamber saturated with 5% carbon dioxide and steam. To the medium was added a series of diluted cytotrienin I, II, III and IV. After 17 hours, MTT reagent was added and growth was measured. The result was shown in Table 10.

TABLE 10

Inhibitory effect of cytotrienins I, II, III and IV
on proliferation of cancel cells IC50 value
[shown as concentration to inhibit 50% of proliferation (µg/ml)]

| Tested cells | Cytotrienins | | | |
|---|---|---|---|---|
| | I | II | III | IV |
| K-562 | 0.02 | 0.005 | 0.005 | 0.001 |
| HL-60 | 0.005 | 0.005 | 0.001 | 0.001 |

K562: Human chronic myelogenic leukemia cells
HL-60: Human acute promyelogenic leukemia cells Table 10 shows that cytotrienins I, II, III and IV are effective as anti-tumor agent.

Evaluation Study 4

Antimicrobial activity of cytotrienins I, II, III and IV

Cytotrienins I, II, III and IV were assayed by the agar dilution method in bouillon medium (examined microorganism; bacteria, 37° C., 1 day) and Sabouraud's medium (examined microorganism: fungus, 28° C., 2 days). Minimum inhibitory concentration is shown in Table 11.

TABLE 11

Antimicrobial activity of cytotrienins I, II, III and IV
(shown as minimum inhibitory concentration (MIC: µg/ml))

| microorganisms | Cytotrienins | | | |
|---|---|---|---|---|
| | I | II | III | IV |
| *Staphylococcus aureus* | >100 | >100 | >100 | >100 |
| *Escherichia coli* BE1186 | >100 | >100 | >100 | >100 |
| *Pseudomonas aeruginosa* | >100 | >100 | >100 | >100 |
| *Pyricularia oryzae* | 12.5 | 12.5 | 12.5 | 12.5 |
| *Candida albicans* | >100 | >100 | >100 | >100 |
| *Chlorella vulgaris* | >100 | >100 | >100 | >100 |

Preparation Example 1 (for injections and drips)

Ten milligrams of cytotrienin I, II, III and IV with 5 g of powdered dextrose was weighed and sealed aseptically in a vial. The vial was filled with inert gas such as nitrogen and helium and kept in a cool and dark space.

When it is used, the compound in the vial is dissolved in ethanol and 0.85% of physiological saline (100 ml) is added to the solution to form a preparation for intravenous injection, 10 to 100 ml/day of which is administered by intravenous injection or drip infusion according to the symptom of the disease.

Preparation Example 2 (granules)

One gram of cytotrienin I, II, III and IV, 98 g of lactose and 1 g of hydroxypropylcellulose were combined and then formed into granular formulation according to the conventional method, followed by being dried to obtain granules, which may be suited to be packed in a vial or heat-sealed. The granules can be orally administered in the amount of 100 to 1000 mg/days.

What is claimed is:

1. A compound having one of the following formulae:

2. The compound of claim 1, which is cytotrienin I.
3. The compound of claim 1, which is cytotrienin II.
4. The compound of claim 1, which is cytotrienin III.
5. A method of preparing cytotrienin I, II or III, comprising a) culturing a bacterium which produces cytotrienin I, II or III which belongs to a species of the genus Streptomyces in a medium, b) accumulating cytotrienin I, II or III in the medium, and c) harvesting cytotrienin I, II or III therefrom.
6. The method of claim 5, wherein the bacterium producing cytotrienin I, II or III is Streptomyces sp 95-74 strain.
7. A pharmaceutical composition, comprising an effective amount of at least one compound selected from the group consisting of cyclotrienin I, II and III, as claimed in claim 1, as an active ingredient; and a carrier.
8. The composition of claim 7, which is in the form of a solid.
9. The composition of claim 7, which is in the form of a liquid solution.
10. The composition of claim 9, wherein said solution is an organic solvent solution or aqueous/organic solvent solution.
11. A method of treating a microorganism infection in a mammal, which comprises administering to said mammal in need thereof an effective amount of one or more of the compounds of claim 1.
12. The method of claim 11, wherein said mammal is a human.
13. The method of claim 11, wherein said microorganism is a bacterium.
14. The method of claim 11, wherein said microorganism is a yeast.
15. A method of treating lung cancer, breast cancer or leukemia in a mammal in need thereof, which comprises administering to said mammal an effective amount of one or more of the compounds of claim 1.
16. The method of claim 15, wherein said mammal is a human.

* * * * *